United States Patent
Cui et al.

(10) Patent No.: US 10,314,491 B2
(45) Date of Patent: Jun. 11, 2019

(54) OPTICS FOR APODIZING AN OPTICAL IMAGING PROBE BEAM

(71) Applicant: The General Hospital Corporation, Boston, MA (US)

(72) Inventors: Dongyao Cui, Boston, MA (US); Kengyeh K. Chu, Boston, MA (US); Guillermo J. Tearney, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/894,574

(22) Filed: Feb. 12, 2018

(65) Prior Publication Data

US 2018/0228374 A1    Aug. 16, 2018

Related U.S. Application Data

(60) Provisional application No. 62/457,882, filed on Feb. 11, 2017.

(51) Int. Cl.
*A61B 1/00* (2006.01)
*A61B 1/05* (2006.01)
(Continued)

(52) U.S. Cl.
CPC ........ *A61B 5/0066* (2013.01); *A61B 1/00112* (2013.01); *A61B 1/00131* (2013.01);
(Continued)

(58) Field of Classification Search
CPC ... A61B 5/0066; A61B 5/0084; A61B 5/0086; A61B 1/00112; A61B 1/00131; A61B 1/00147; A61B 1/051; G01B 9/02015; G01B 9/02091; G01N 2021/015; G02B 6/32; G02B 6/26; G02B 6/0096; G02B 6/322

See application file for complete search history.

(56) References Cited

U.S. PATENT DOCUMENTS 6,501,551 B1 * 12/2002 Tearney ............. A61B 1/00096
                                                    356/477
9,574,870 B2 * 2/2017 Yamazaki ............ A61B 5/0066
(Continued)

OTHER PUBLICATIONS

Tumlinson et al. "Endoscope-tip interferometer for ultrahigh resolution frequency domain optical coherence tomography in mouse colon" Mar. 6, 2006 / vol. 14, No. 5 / Optics Express 1881 (Year: 2006).*

(Continued)

*Primary Examiner* — Dominic J Bologna
(74) *Attorney, Agent, or Firm* — Quarles & Brady LLP

(57) ABSTRACT

Optics for apodizing an optical imaging probe beam, and methods for fabricating optics for apodizing an optical imaging probe beam are provided. In some embodiments, optics for apodizing an electrical comprises: an optical fiber; a focusing element coaxially aligned with the optical fiber; an element having a cylindrical bore and an angled reflective surface, wherein a first portion of a beam focused by the focusing element enters the cylindrical bore and a second portion of the beam is reflected at an angle to produce a beam with a generally annular-shaped profile.

20 Claims, 8 Drawing Sheets

(51) Int. Cl.
    A61B 5/00      (2006.01)
    G01B 9/02      (2006.01)
    G01N 21/01     (2006.01)
    G02B 6/32      (2006.01)

(52) U.S. Cl.
    CPC .......... *A61B 1/00147* (2013.01); *A61B 1/051* (2013.01); *A61B 5/0084* (2013.01); *A61B 5/0086* (2013.01); *G01B 9/02015* (2013.01); *G01B 9/02091* (2013.01); *G02B 6/32* (2013.01); *G01N 2021/015* (2013.01)

(56) References Cited

U.S. PATENT DOCUMENTS

| | | | |
|---|---|---|---|
| 2013/0216114 A1* | 8/2013 | Courtney | A61B 5/0066 382/128 |
| 2014/0160482 A1* | 6/2014 | Tearney | G01B 9/02044 356/451 |
| 2017/0027645 A1* | 2/2017 | Ben Oren | A61B 6/00 |
| 2017/0370699 A1* | 12/2017 | Hogan | G01B 9/02059 |
| 2018/0045501 A1* | 2/2018 | Elmaanaoui | G01B 9/02015 |

OTHER PUBLICATIONS

Chu et al. "In vivo imaging of airway cilia and mucus clearance with micro-optical coherence tomography" Jul. 1, 2016 | vol. 7, No. 7 | DOI:10.1364/BOE.7.002494 | Biomedical Optics Express 2497 (Year: 2016).*

Liu et al. "Method for Quantitative Study of Airway Functional Microanatomy Using Micro-Optical Coherence Tomography" PLOS One Jan. 1, 2013 | vol. 8 | Issue 1 | e54473 (Year: 2013).*

* cited by examiner

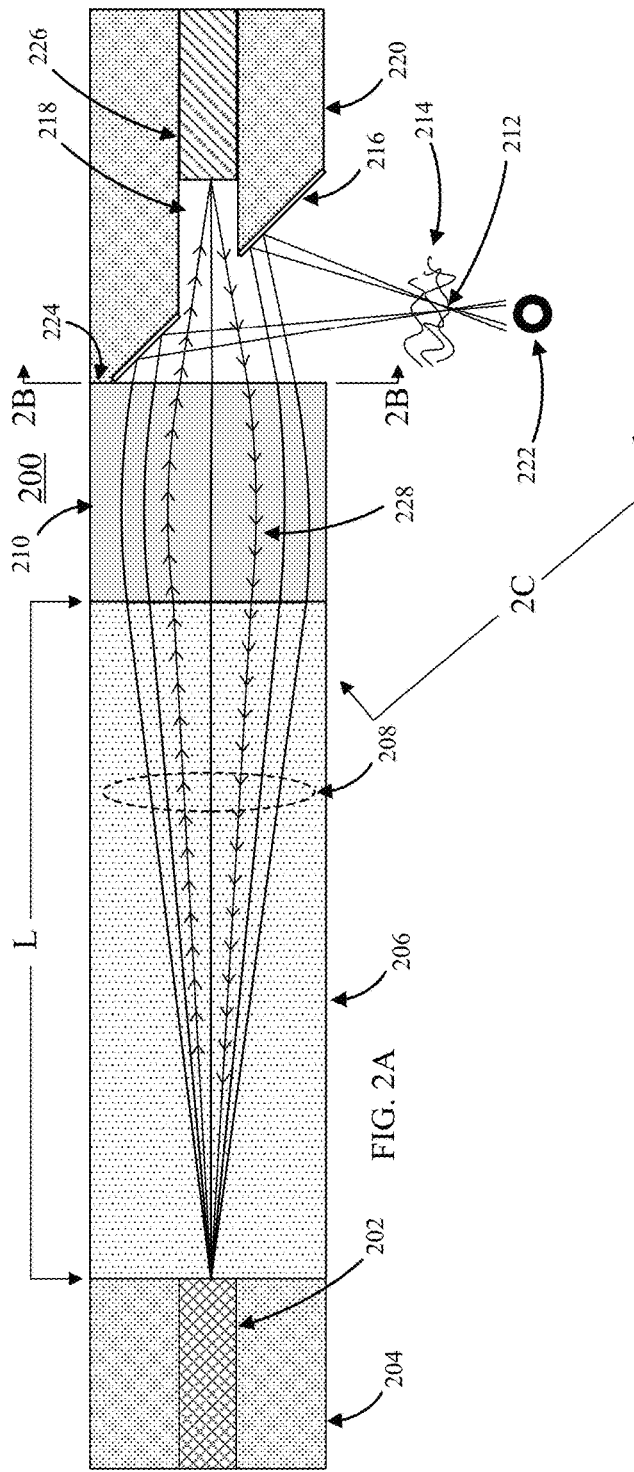
FIG. 2A
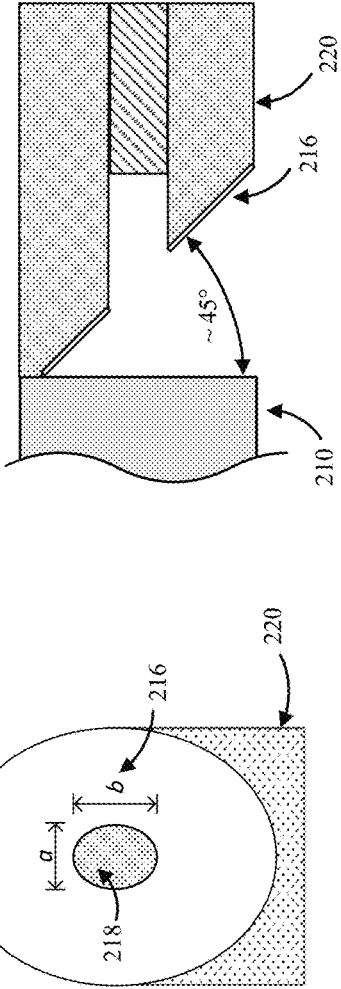
FIG. 2D
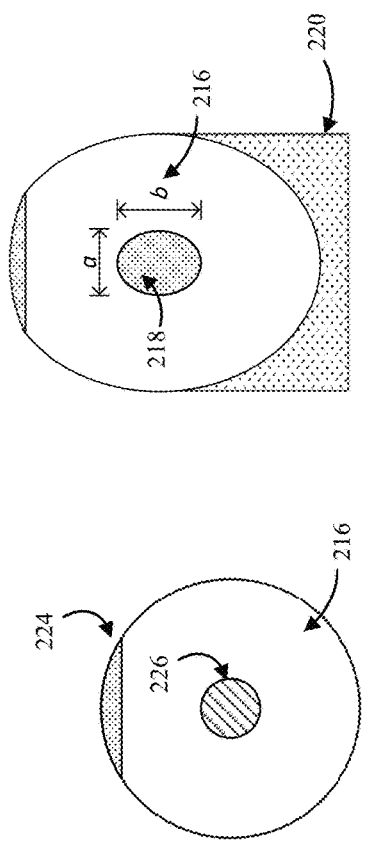
FIG. 2C
FIG. 2B

OPTICS FOR APODIZING AN OPTICAL IMAGING PROBE BEAM

CROSS-REFERENCE TO RELATED APPLICATIONS

This application is based on, and claims the benefit of U.S. Provisional Patent Application No. 62/457,882, filed Feb. 11, 2017, which is hereby incorporated herein by reference in its entirety for all purposes.

STATEMENT REGARDING FEDERALLY SPONSORED RESEARCH

This invention was made with government support under grant number HL116213 awarded by the National Institutes of Health. The government has certain rights in the invention.

BACKGROUND

Many microscopic imaging systems project a beam of light onto a sample, and generate images based on light received from the sample. In many imaging devices that scan a sample with an illumination beam (sometimes referred to herein as optical beam scanning systems), the amount of information that can be reliably gathered using such systems is often related to the shape and/or other physical characteristics of the beam. Various imaging systems utilize such a scanning illumination beam. For example, confocal microscopy systems focus a beam of light at a particular lateral location (e.g., in the x-y plane), and at a particular depth (e.g., in the z plane). By scanning a portion of the sample in two dimensions at various depths, data collected by the confocal microscopy system can be used to generate three-dimensional images that include subsurface features. Confocal microscopy systems are often used to scan ex vivo samples that can be placed on a stage, and the beam is scanned over the x-y plane parallel to the surface of the stage, and the beam is focused at various depths, for example, by changing the focal length of an optical system used to focus the beam on the sample.

In many imaging modalities that utilize optical beam scanning, the lateral resolution is related to the lateral size of the focused beam (i.e., how tightly the beam is focused), which imposes a limit on the system's ability to resolve small features in the direction perpendicular to the direction of travel of the beam. In such systems, the more tightly the beam is focused, the more resolving power the system generally has in the lateral direction. In general, as a beam is more tightly focused in the lateral direction the depth of focus (DOF) of the beam also becomes smaller. That is, it is difficult to create a beam with a tight focus laterally that is also relatively elongated in the depth direction. In general, in known devices such as cameras and projectors, the DOF is the difference between the farthest point from the lens (or other focusing optics) at which an image projected by the lens is considered in focus and the nearest point from the lens at which the image is considered in focus. For example, the imaging medium (e.g., image sensor or film) of a camera is within the DOF of the lens when the image captured by the imaging medium is in focus (note that this is assuming that the object(s) being imaged is within the depth of field of the optical system). Similarly, an image projected by a projector is within the DOF of the lens if the projected image is in focus. In such systems, one portion of an imaging medium or projection surface may be within the DOF while another part may be outside the DOF (e.g., because the imaging medium/screen may be tilted with respect to the optical axis). The DOF of a beam in an optical beam scanning an imaging system, however, is the range of depths over which features can be resolved by the imaging system. Accordingly, there is generally a relationship between the DOF of the beam and how tightly the beam is focused laterally. For example, as the beam becomes more tightly focused to increase lateral resolution, optical diffraction generally causes the beam to converge to the focal point, and to diverge from the focal point at larger angles, causing the range of depths over which features can be resolved to be smaller. Conversely, when the beam converges to the focal point at a shallower angle, the DOF increases, but this also generally results in lower lateral resolution.

In some imaging modalities, such as confocal microscopy, a small DOF is generally believed to be beneficial, as the system focuses the beam at various depths during scanning resulting in the ability to resolve smaller features in the depth direction. In such imaging systems, the axial resolution (e.g., the ability to resolve small objects in the direction aligned with the travel of the beam) is likely identical to the DOF, as the rapid loss of focus away from the focal plane prevents objects in other planes from spuriously contributing to the imaging of the focal plane itself. Accordingly, in such systems, a more tightly focused beam likely increases the maximum lateral resolution and axial resolution.

However, in other imaging modalities, such as optical coherence tomography (OCT), axial resolution is derived from the depth-ranging capability of the modality itself. That is, because OCT systems can simultaneously detect and separate signals from varying depths without changing the focal length of the beam optics, it is generally more desirable to use a beam with a large DOF, so that more depths may be simultaneously captured in a single pass. However, because of the relationship between the lateral tightness of the focus and DOF, high lateral resolution generally comes at the expense of DOF, and vice-versa. Conventional OCT techniques generally produce images of tissue reflectance with resolutions of approximately 10 micrometers ($\mu m$) axially and 30 $\mu m$ laterally, which can generally facilitate visualization of microscopic architectural morphology, but is insufficient for resolving individual human cells, which are typically on the order of 10 $\mu m$ in size.

SUMMARY

Accordingly, new optics for apodizing an optical imaging probe beam are desirable.

In accordance with some embodiments of the disclosed subject matter, optics for apodizing an optical imaging probe beam are provided.

In accordance with some embodiments of the disclosed subject matter, optics for apodizing an optical imaging probe beam are provided, the optics comprising: an optical fiber; a focusing element coaxially aligned with the optical fiber; and an element having a cylindrical bore and an angled reflective surface, a first portion of a beam being focused by the focusing element and entering the cylindrical bore, and a second portion of the beam being reflected at an angle by the angled reflective surface to produce a beam with a generally annular-shaped profile.

In some embodiments, the focusing element is a cylindrical gradient index lens.

In some embodiments, the element having the cylindrical bore comprises a ferrule, wherein the angled reflective surface comprises a polished surface.

In some embodiments, the ferrule is ceramic.

In some embodiments, the angled reflective surface comprises a reflective coating.

In some embodiments, the reflective coating comprises gold.

In some embodiments, the optics further comprise a spacer disposed between the optical fiber and the focusing element, wherein the beam expands in diameter within the spacer.

In some embodiments, the spacer comprises glass.

In some embodiments, the optical fiber is disposed within a ferrule.

In some embodiments, a reflective surface is disposed within the cylindrical bore to reflect the first portion of the beam back toward the optical fiber.

In some embodiments, the reflective surface comprises a face of a second optical fiber disposed within the cylindrical bore.

In accordance with some embodiments of the disclosed subject matter, an OCT imaging system is provided, the system comprising: a reference arm; a light source; and apodizing optics for generating an apodized beam comprising: an optical fiber coupled to the light source, a focusing element coaxially aligned with the optical fiber, and a cylindrical element coaxially aligned with the focusing element, the cylindrical element having a bore and an angled reflective surface, a first portion of a beam being focused by the focusing element and entering the bore, and a second portion of the beam being reflected at an angle by the angled reflective surface to produce a beam with a generally annular-shaped profile.

In some embodiments, the reference arm comprises a reference reflective surface disposed within the bore to reflect the first portion of the beam back toward the optical fiber.

In some embodiments, the angled reflective surface is at a 45 degree angle with respect to a long axis of the cylindrical element.

In some embodiments, the focusing element is a cylindrical GRIN lens.

In some embodiments, the angled reflective surface comprises a reflective coating.

In some embodiments, the optics are rotatably mounted within the OCT imaging system.

In some embodiments, the OCT system further comprises a catheter including the apodizing optics.

In some embodiments, the OCT system further comprises a spacer disposed between the optical fiber and the focusing element, wherein the beam expands in diameter within the spacer.

In some embodiments, the cylindrical element further comprises a truncated face which abuts the focusing element.

In accordance with some embodiments of the disclosed subject matter, a method for fabricating optics for apodizing an optical imaging probe beam is provided, the method comprising: providing a ferrule comprising: a first face at a first end, a second face at a second end, wherein the second face is substantially parallel to the first face and substantially perpendicular to a central axis of the ferrule, and a cylindrical bore passing between the first face and the second face; polishing the first end of the ferrule at an angle to create a third face at an angle of between about 40 degrees and about 50 degrees with respect to an original face of the ferrule; coaxially aligning the cylindrical bore with an optical fiber and a focusing element such that a beam exiting the optical fiber is focused by the focusing element toward the third face, wherein a first portion of the beam focused by the focusing element enters the cylindrical bore and a second portion of the beam is reflected at an angle by the third face to produce a beam with a generally annular-shaped profile; and coupling the polished ferrule to the focusing element.

In some embodiments, the focusing element is a cylindrical gradient index lens.

In some embodiments, the method further comprises applying a reflective coating to the third face prior to coaxially aligning the cylindrical bore with an optical fiber and a focusing element.

In some embodiments, the reflective coating comprises gold.

In some embodiments, the method further comprises coupling a spacer between the focusing element and the optical fiber, wherein the spacer allows the beam exiting a face of the optical fiber to expand in diameter before reaching the focusing element.

In some embodiments, the optical fiber is disposed within a second ferrule, and the method further comprises coupling the spacer to the second ferrule.

In some embodiments, the method further comprises positioning a reflective surface within the cylindrical bore to reflect the first portion of the beam back toward the optical fiber to act as a reference beam for an optical coherence tomography imaging device.

In some embodiments, the reflective surface is a face of a second optical fiber disposed within the cylindrical bore.

In some embodiments, the method further comprises: adjusting the position of the reflective surface; monitoring a path length of a reference beam created by the reflective surface; determining, based on the path length, that the path length of the reference beam is substantially equal to a path length of a sample beam; and in response to determining that the path length of the reference beam is substantially equal to the path length of the sample beam, securing the reflective surface within the cylindrical bore at the position at which the path lengths are substantially equal.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 2A shows an example of a cross-section view of optics that can be used for apodizing an optical imaging probe beam in accordance with some embodiments of the disclosed subject matter.

FIG. 2B shows an example of a plan view of a portion of the optics of FIG. 2A in accordance with some embodiments of the disclosed subject matter.

FIG. 2C shows an example of another view of a portion of the optics of FIG. 2A in accordance with some embodiments of the disclosed subject matter.

FIG. 2D shows an example of an angle of the angled reflective surface of the optics of FIG. 2A in accordance with some embodiments of the disclosed subject matter.

DETAILED DESCRIPTION

Figure 1:
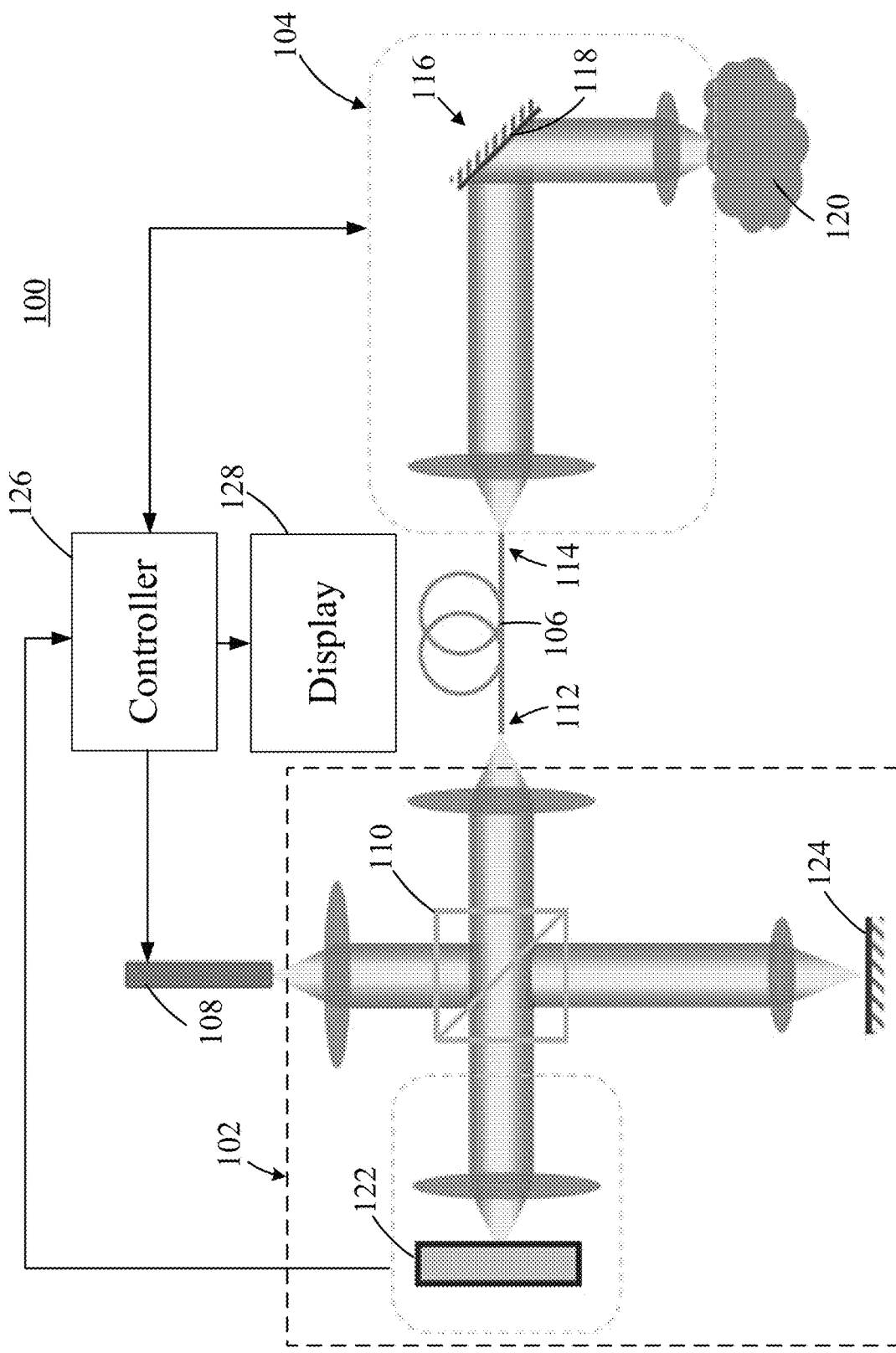
FIG. 1 shows an example of an optical coherence tomography system with an optical imaging probe using conventional optics.

In accordance with some embodiments of the disclosed subject matter, mechanisms (which can include, for example, systems, devices, methods of use, and methods of fabrication) for apodizing an optical imaging probe beam are provided.

In some embodiments, mechanisms described herein can be used to implement compact optics that generate and provide a beam with a circular obscuration. In some embodiments, the mechanisms described can include an optical waveguide (e.g., an optical fiber, a bundle of optical fibers, etc.) that can receive light from a light source (e.g., a broadband light source), and can conduct the light toward the optical imaging probe.

In some embodiments, a relatively compact focusing element, such as a GRIN lens, can be positioned between the distal (relative to a light source) end of the waveguide and a reflective surface that diverts a beam of light that exits the optical waveguide toward a sample. The compact focusing element can focus the beam of light (e.g., as from a point-like source, such as a face of an optical fiber, or a pinhole) at (or near) the surface of a sample.

In some embodiments, the mechanisms described herein can include a cylindrical element having a cylindrical hollow space at its center. In some such embodiments, a portion of the cylindrical element can be removed (e.g., by polishing) to create an angled face that can be placed in the path of the beam to divert the beam from an axis of the focusing element toward a surface of a sample (e.g., tissue of a luminal passageway of an organ). In some embodiments, the beam that is reflected from the cylindrical element can have an annular shape, as a portion of the beam passes into the cylindrical hollow, while the surrounding portion of the beam is deflected toward the sample.

In some embodiments, the mechanisms described herein can include a reflector placed within the cylindrical hollow to reflect at least a portion of the light that passed into the cylindrical hollow back toward an optical imaging system coupled to the optical waveguide. In some embodiments, the reflector can be positioned to provide a reference signal for an OCT system.

In some embodiments, the mechanisms can include an optical spacer that facilitates expansion of light exiting a face of the optical waveguide to provide a beam with a relatively large cross-sectional area. Additionally or alternatively, in some embodiments, a space between the face of the optical waveguide and the focusing element can be provided, in whole or in part, by a gap filled with air, another gas(es), a liquid, a gel, or other non-solid medium.

In some embodiments, the mechanisms can include a cylindrical tube that can securely enclose at least a portion of the optical elements used to create an annular beam. In some embodiments, such a cylindrical tube can facilitate coaxial alignment of various optical components (e.g., the optical waveguide, the focusing element, and the polished cylindrical element), and/or maintain an alignment of the optical elements.

In various embodiments, the disclosed apodized optical imaging probe beam may be used with imaging systems such as optical coherence tomography (OCT) systems, described further below. OCT systems focus a beam of light at a particular lateral location and capture information from light reflected at various depths at that location without varying the focal plane of the OCT system, by detecting interference between the light reflected from the sample and light reflected from a reference reflector. This allows an OCT system to collect data from multiple depths at each laterally-scanned location. OCT systems may be used to collect information in vivo, from a living subject. For example, some OCT systems use a rotating beam to scan the tissue around the circumference of a probe that can be inserted into a luminal sample such as an airway, esophagus, etc., of the subject, and the probe moves laterally as the beam is scanned around the circumference without changing the focal length of the optical system used to focus the beam on the sample.

A compact form factor for creating such an annular beam may be necessary for in vivo medical imaging (e.g. for use with a catheter or swallowable capsule). One approach to miniaturization that has been implemented has been to use a gradient-index (GRIN) lens and a manually-patterned prism to create an annular beam, involving applying a round spot of epoxy to the hypotenuse face of a right-angle prism. The hypotenuse face may be coated with a reflective metal coating and the epoxy dot may be removed, leaving a transmissive center such that a beam reflected from the hypotenuse can potentially be missing its center, resulting in an annular beam. However, this technique may be limited in the precision of the annular beam it can create, and may be difficult to precisely align. Additionally, because the epoxy spot is circular but the beam intersects the transmissive aperture at a 45 degree angle, the resulting obscuration on the reflected beam using this approach is elliptical rather than circular, which results in unequal enhancement of DOF in the lateral dimensions.

Though the relationship between lateral resolution and DOF cannot be overcome to independently maximize both lateral resolution and axial resolution in an OCT system, the shape of the beam being focused can significantly enlarge the DOF for a given lateral resolution, or conversely improve lateral resolution for a given DOF. For example, an annular beam can provide a larger DOF for a given lateral resolution. One approach that has been proposed for creating an annular beam for OCT systems has been to create a circular obscuration at the center of an otherwise Gaussian-shaped beam profile. One such approach has been implemented (e.g., for a micro-OCT (µOCT) system) using a rod mirror placed in the path of the beam in a bench-top system, which was able to resolve cellular and sub-cellular microstructures of biological tissues. Nevertheless, such a system is not practical for use with in vivo applications.

Accordingly, mechanisms for producing an apodized optical imaging probe beam are provided herein which are suitable for numerous applications, including OCT/µOCT and in vivo/medical applications.

FIG. 1 shows an example 100 of an OCT system with an optical imaging probe using conventional optics which may be adapted for use with an apodized optical imaging probe beam as disclosed herein. As shown in FIG. 1, optical system 100 includes an external optical assembly 102 optically coupled to an optical imaging probe 104 via an optical waveguide 106 (e.g., an optical fiber, an optical fiber bundle, separate optical fibers, etc.). Optical imaging probe 104 may take various forms, for example it may be incorporated into a catheter or a tethered capsule for imaging structures such as a luminal sample (e.g. in the vascular, pulmonary, or gastrointestinal systems) in a subject such as a human. In optical system 100, external optical assembly 102 is configured to receive source light from a light source 108, and includes a beam splitter 110 to reflect a portion of the source light into a distal end 112 of the optical waveguide 106, and another portion of the source light onto a reference reflector 124. In the OCT system of FIG. 1, light source 108 can be a broadband light source, such as a broadband laser configured to sweep wavelengths in the near-infrared spectrum.

Optical waveguide 106 of optical system 100 is configured to efficiently transmit the source light from distal end 112 to a distal end 114, which is coupled to optical imaging probe 104 and arranged to project the source light from distal end 114 onto an optical component 116 within optical imaging probe 104. Optical component 116 can be implemented with a reflective surface 118 configured to efficiently reflect the source light emitted from distal end 114 of optical waveguide 106 onto a sample 120 (e.g., a portion of a luminal organ or tissue within a patient).

In optical system 100, distal end 114 of optical waveguide 106 is arranged to receive reflected light from sample 120 via reflective surface 118. The reflected light is then transmitted along optical waveguide 106 from distal end 114 to proximal end 112. Light reflected from sample 120 that is transmitted to proximal end 112 of optical waveguide 106 is then transmitted through beam splitter 110 to an optical detector 122, such as a CCD image sensor, a CMOS image sensor, photodiodes (made of Silicon, Germanium, InGaAs, Lead sulfide, or other materials), photocells, photoresistors, phototransistors, etc. As described above, a portion of the source light output by light source 108 was transmitted through beam splitter 110 to reference reflector 124, which reflects the incident light and directs it back to beam splitter 110, which reflects the reference light to optical detector 122 such that optical detector 122 receives both reference source light reflected from reference reflector 124 and light reflected off reflective surface 118 from sample 120. Interference (e.g., constructive and/or destructive interference) between the reference light and the light reflected from sample 120 allows discrimination between signals from different depths, as constructive interference between the reference signal and sample signal indicates that the signals have traveled equivalent distances, and the depth of a particular received signal can be calculated based on the interference of the signals.

A controller 126 can coordinate operation of one or more of optical imaging probe 104, light source 108, optical detector 122, and a display 128. Controller 126 can be in wired (e.g., via Ethernet, USB, CAN, etc.) and/or wireless (e.g., via Bluetooth®, WiFi, etc.) communication with optical imaging probe 104, the light source 108, the optical detector 122, and/or the display 128.

In optical system 100, controller 126 reconstructs the reflected light off reflective surface 118 from sample 120 that is detected by optical detector 122 into cross-sectional morphological data. For example, optical system 100 can use an optical frequency domain imaging technique or combination of techniques to generate the cross-sectional morphological data, and can generate a three-dimensional representation (e.g., of a portion of a luminal organ or passageway of a patient) by combining information from sequential cross-sections.

FIG. 2A shows an example 200 of a cross-section view of optics that can be used for apodizing an optical imaging probe beam in accordance with some embodiments of the disclosed subject matter. As shown in FIG. 2A, optics 200 can include an optical fiber 202, which can be secured within a ferrule 204, which can be used to support and align optical fiber 202 at an intersection between optical fiber 202 and a spacer 206.

In some embodiments, spacer 206 can be made from a transparent material (e.g., glass, plastic, etc.), a gas (e.g., air, nitrogen, etc.), a gel, a liquid, etc. In some embodiments, spacer 206 can have a length L to allow a beam 208 to expand to a desired radius from the radius at which it exits the face of optical fiber 202.

In some embodiments, optics 200 can include a focusing element 210 to focus beam 208 toward a focal point 212. In some embodiments, focusing element 210 can be any suitably compact focusing element, such as a GRIN lens. In some embodiments, focal point 212 can be set at a distance from focusing element 210 to be located near a tissue sample 214 to be sampled.

In some embodiments, optics 200 can include an angled reflective surface 216 that diverts beam 208 toward sample 214. In some embodiments, angled reflective surface 216 can include an aperture 218 into which a portion of beam 208 is directed, rather than being diverted toward sample 214. In some embodiments, angled reflective surface 216 can be any suitable reflective material that reflects substantially all of beam 208 that impinges on the surface of angled reflective surface 216. For example, in some embodiments, angled reflective surface 216 can be made from a reflective coating (e.g., gold or another reflective material) applied to an angled surface of a hollow element 220 that has been polished to provide an angled surface. Additionally or alternatively, in some embodiments, hollow element 220 can be made from a material that reflects a sufficient amount of light at wavelengths included in beam 208 and/or wavelengths that are used in a particular imaging procedure.

In some embodiments, hollow element 220 can be any suitable hollow element, such as a ferrule manufactured from glass or ceramic with a hollow core that is sized to receive an optical fiber (e.g., for use in an optical fiber connector). Due to their use in many fiber optic applications, ferrules are generally widely available at relatively low cost. In some such embodiments, hollow element 220 can be manufactured to include aperture 218 (e.g., when a ferrule is used as hollow element 220). Alternatively, in some embodiments, aperture 218 can be created from a solid element (e.g., by machining, etching, etc.).

In some embodiments, hollow element 220 can be manufactured with an angled surface. Additionally or alternatively, in some embodiments, a portion of hollow element 220 can be removed to create a reflective surface at a desired angle. For example, a portion of a ferrule can be polished at the desired angle to create a substrate to which a reflective coating is applied to create angled reflective surface 216. In some embodiments, angled reflective surface 216 can be at any suitable angle to an axis of beam 208 such that, when hollow element 220 is coaxially aligned with optical fiber 202 and focusing element 210, the path of beam 208 is diverted approximately 90 degrees toward sample 212. For example, angled reflective surface 216 can be manufactured to form an angle of approximately 45 degrees with a surface of focusing element 210 (e.g., when focusing element 210 is a GRIN lens with flat ends). In some embodiments, angled reflective surface 216 can be manufactured with an angle that deviates from 45 degrees (e.g., by zero to five degrees) to reflect beam 208 at angle that is shallower or sharper than 90 degrees, which can be desirable in some circumstances to avoid bright specular reflections from surfaces that are directly normal to a beam reflected at 90 degrees.

Note that, due to the angle of angled reflective surface 216, the intersection of the aperture 218 with the angled face can form an ellipse when viewed from an angle normal to angled reflective surface 216, or from an angle normal to the plane of reflective surface 216 (e.g., as shown in FIG. 2C). However, the projection of aperture 218 onto input beam 208 can remain circular, since its axis is aligned with the direction of propagation of beam 208. For example, as shown in plan view FIG. 2B, when viewed from an angle normal to the plane at which focusing element 210 meets hollow element 220, aperture 218 presents as a circular aperture. Accordingly, the reflected beam generally exhibits a circular, rather than ellipsoidal, obscuration, resulting in a beam with an annular profile 222. Note that this type of beam shaping is sometimes referred to as apodization, and a reflector configured as described above is sometimes referred to herein as an Angle-Polished Apodizing Reflector (APAR).

As shown in FIG. 2A, in some embodiments, hollow element 220 can have a face 224 at which hollow element 220 can abut focusing element 210. The length of face 224 in the radial direction can be based on the radius of beam 208 when it intersects angled reflective surface 216. For example, face 224 can be sized so that beam 208 does not intersect face 224. In some embodiments, truncating hollow element 220 at face 224 (e.g., rather than angled reflective surface 216 extending over the entire diameter of hollow element 220) can reduce the overall length of optics 200, and provide a flat surface for aligning and/or securing hollow element 220 and focusing element 210 (e.g., using an optical adhesive). Note that, in some embodiments, hollow element 220 and focusing element 210 can be aligned without abutting one another (e.g., by an alignment element, not shown in FIGS. 2A to 2C).

In some embodiments, a reference reflector 226 can be provided within aperture 218 to provide a reference beam that can be used in, for example, OCT. In OCT, information is extracted from the sample beam through interference with a reference beam (e.g., of approximately an equal path length). Reference reflector 226 can be used to generate the reference beam within the same optical configuration (e.g., without a separate reference arm, as shown in FIG. 1). In some embodiments, the portion of beam 208 that enters aperture 218 can be reflected by reference reflector 226. For example, as shown in FIG. 2A, while the portion of beam 208 that intersects angled reflective surface 216 is diverted toward sample 214, a portion that enters aperture 218 is reflected off of reference reflector 226 (e.g., as shown, a ray 228 can be reflected back through focusing element 210 and focused on a face of optical fiber 202). In some embodiments, reference reflector 226 can be implemented by inserting and securing an element (e.g., an optical fiber) that is configured to have a reflective face (e.g., by polishing, by coating with a reflective coating, etc.) into aperture 218. In some embodiments, for example, when hollow member 220 is implemented using a ferrule, aperture 218 can be manufactured with a size that is configured to receive an optical fiber without modification. In some embodiments, reference reflector 226 can be an integral part of hollow element 220 (e.g., when aperture 218 is made by machining or otherwise removing a portion of material to create aperture 218).

In some embodiments, reference reflector 226 can be positioned within aperture 218 to provide an appropriate path length for a reference signal. For example, as described below in connection with FIG. 7, reference reflector 226 can be positioned while providing a beam through optics 200 and monitoring an interference signal between a sample signal and a reference beam reflected by reference reflector 226 in real-time. In such an example, when the path length of reference reflector 226 is positioned to provide a reference beam, the position of reference reflector 226 can be secured within aperture 218. Reference reflector 226 can be secured using any suitable technique or combination of techniques, such as using an ultraviolet (UV)-curing adhesive that can be set by exposing the adhesive to UV radiation.

Note that, in some embodiments, if a reference signal is provided externally (e.g., by an external reference reflector, such as reference reflector 124) or for use with imaging modalities that do not use a reference beam, reference reflector 226 can be omitted entirely (and/or replaced with an optical element that absorbs light from the beam), and the portion of beam 208 entering aperture 218 can be disregarded and/or discarded.

FIG. 2B shows a plan view of an example of a portion of the optics of FIG. 2A (i.e., the APAR described above in connection with FIG. 2A) from the perspective shown by arrows labeled '2B' in FIG. 2A, and FIG. 2C shows an example of another view of a portion of the optics of FIG. 2A (i.e., the APAR described above in connection with FIG. 2A) from the perspective shown by arrows labeled '2C' in FIG. 2A (without spacer 206 or focusing element 210), in accordance with some embodiments of the disclosed subject matter. As shown in FIG. 2B, reference reflector 226 can appear to be included within an aperture in angled reflective surface 216 with a circular profile, although, as shown in FIG. 2C, a profile of aperture 218 from a perspective perpendicular to the plane of angled reflective surface 216 appears to be an ellipse with a minor axis (labeled a) that is substantially equal to the diameter of aperture 218, and a (longer) major axis (labeled b). As shown in FIG. 2D, the angle between the surface of focusing element 210 and angled reflective surface 216 of the APAR can be about 45 degrees. Additionally, in some embodiments, such as when hollow element 220 is implemented using a ferrule, the angle between the original face of the ferrule (prior to removal of a portion of the ferrule, e.g., by polishing) and angled reflective surface 216 can be about 45 degrees.

Figure 3:
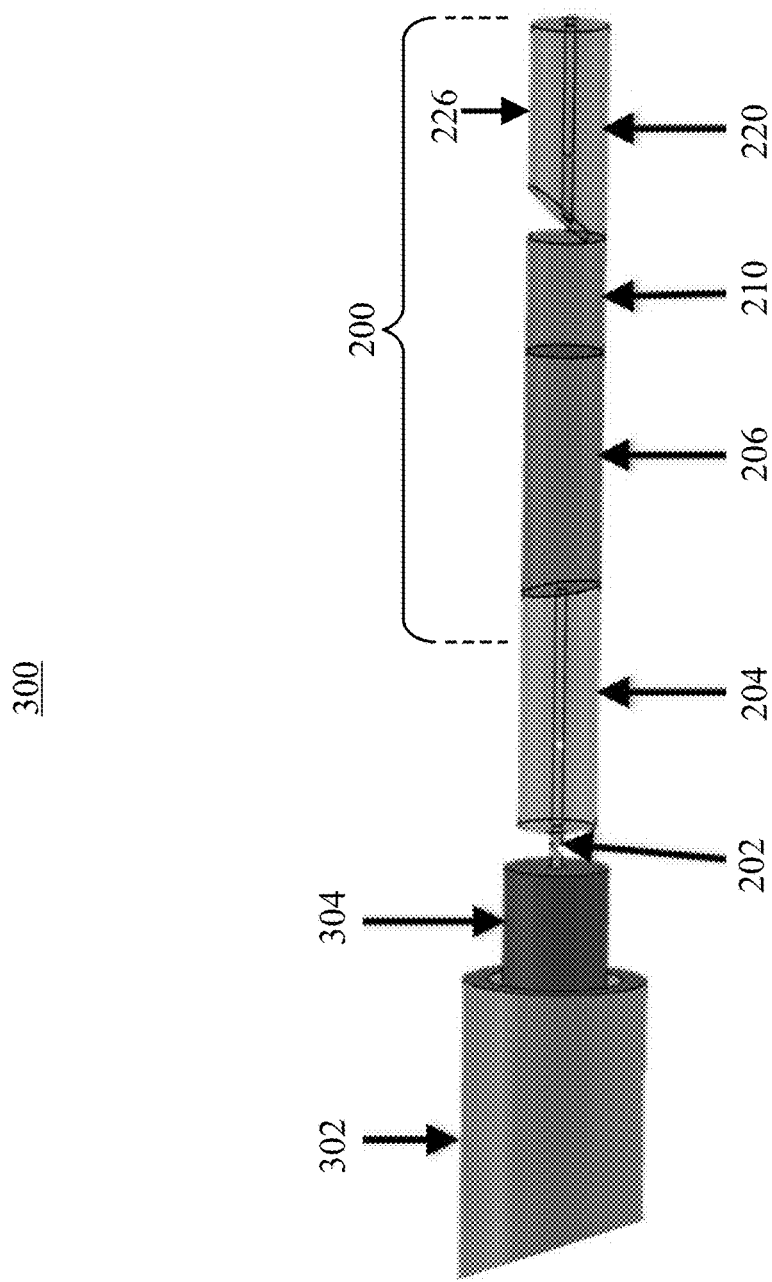
FIG. 3 shows an example of optics that can be used for apodizing an optical imaging probe beam in accordance with some embodiments of the disclosed subject matter.

FIG. 3 shows an example 300 of a portion of an optical imaging probe for OCT that includes optics that can be used for apodizing an optical imaging probe beam in accordance with some embodiments of the disclosed subject matter. As shown in FIG. 3, probe 300 can include an outer tube 302 that can act as an enclosure to align and/or secure other components of probe 300. In some embodiments, outer tube 302 can be any suitable material and/or combination of materials, such as a metal (e.g., steel), glass, ceramic, polymer, etc. In some embodiments, outer tube 302 can form one or more parts of an optical fiber cable, such as a buffer, a strength member, an outer jacket, etc. In some embodiments, an inner tube 304 can provide a mechanical attachment for optical fiber 202 and/or ferrule 204. In some embodiments, inner tube 304 can form one or more parts of an optical fiber, such as a coating, a buffer, a strength member, etc. Additionally or alternatively, inner tube 304 can be a drive shaft for mechanically rotating optical fiber 202, ferrule 204, and/or optics 200. In some embodiments, such a drive shaft can transmit longitudinal and/or rotational force to perform a scanning operation within outer tube 302. Note that this is merely an example, and optics 200 can be used with other optical probes, such as a probe in which ferrule 220 (and potentially other components, such as lens 210) are secured to a motor, and rotated relative to optical fiber 202 and ferrule 204, which remain stationary (e.g., within outer tube 302), for example for use with a tethered optical imaging probe as described in International Patent Application Publication No. WO 2017/059246, which is hereby incorporated by reference herein in its entirety for all purposes. In some embodiments, an optical imaging probe implemented in accordance with some embodiments of the disclosed subject matter (e.g., as described in connection with FIGS. 2A to 2D, and 3) can be used to implement imaging probe 104 of FIG. 1 (e.g., when reference reflector 226 is omitted), and can, in some embodiments, replace reference reflector 124 (e.g., as described below in connection with FIG. 9).

Figure 4:
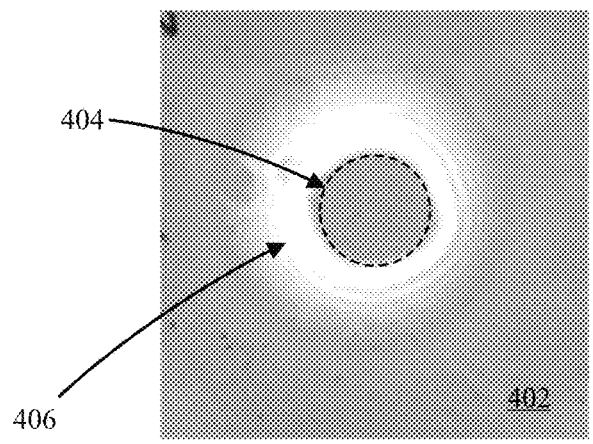
FIG. 4 shows an example of a beam profile that can be created with optics for apodizing an optical imaging probe beam in accordance with some embodiments of the disclosed subject matter.

FIG. 4 shows an example of a beam profile that can be created with optics for apodizing an optical imaging probe beam in accordance with some embodiments of the disclosed subject matter. As shown in FIG. 4, a beam is projected onto a flat surface 402 (e.g., corresponding to sample 214) with the focal point (e.g., focal point 212 of FIG. 2A) between the image sensor and flat surface 402 such that the rays of the annular beam have begun diverging from the focal point when the beam impinges on flat surface 402. FIG. 4 includes a generally circular inner region 404 with very low (or zero) intensity, and a generally circular surrounding region 406 with much higher intensity that falls off with distance from a center axis of the beam (e.g., beam 208). As described above in connection with FIG. 2A, the low-intensity inner region 404 may be created by the absence of the portion of beam 208 that entered aperture 218, and surrounding region 406 may be created by the portions of beam 208 that were reflected by angled reflective surface 216.

Figure 5A:
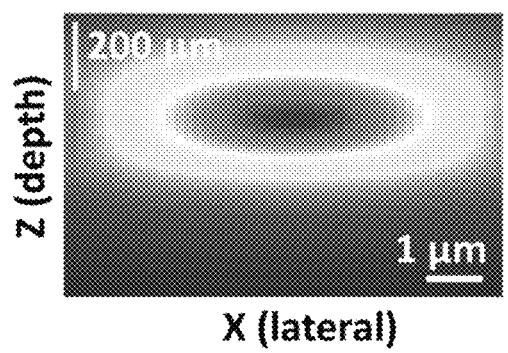
FIG. 5A shows an example of simulated beam intensity on the x-z plane of an optical imaging probe beam created by conventional optics.
Figure 5B:
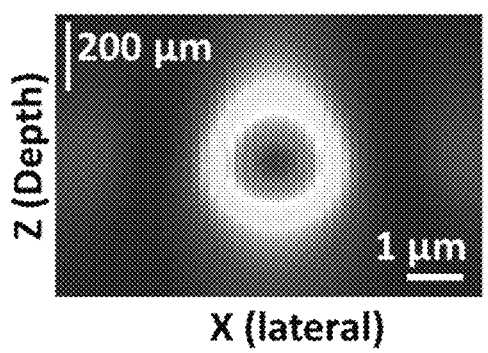
FIG. 5B shows an example of simulated beam intensity on the x-z plane of an optical imaging probe beam created by optics that can be used for apodizing the optical imaging probe beam in accordance with some embodiments of the disclosed subject matter.

FIGS. 5A, 5B show examples of simulated beam intensities on the x-z plane of an optical imaging probe beam that would be created using conventional optics (FIG. 5A) and using apodizing optics, such as the APAR described above in connection with FIG. 2A (FIG. 5B). Comparing the simulated intensity profiles between the two images it can be seen that the depth of focus (Z) in each case is approximately the same but that the intensity profile is significantly smaller in the lateral (X) direction using apodized optics (FIG. 5B) compared to conventional optics (FIG. 5A), indicating a higher lateral resolution using apodized optics.

Figure 6A:
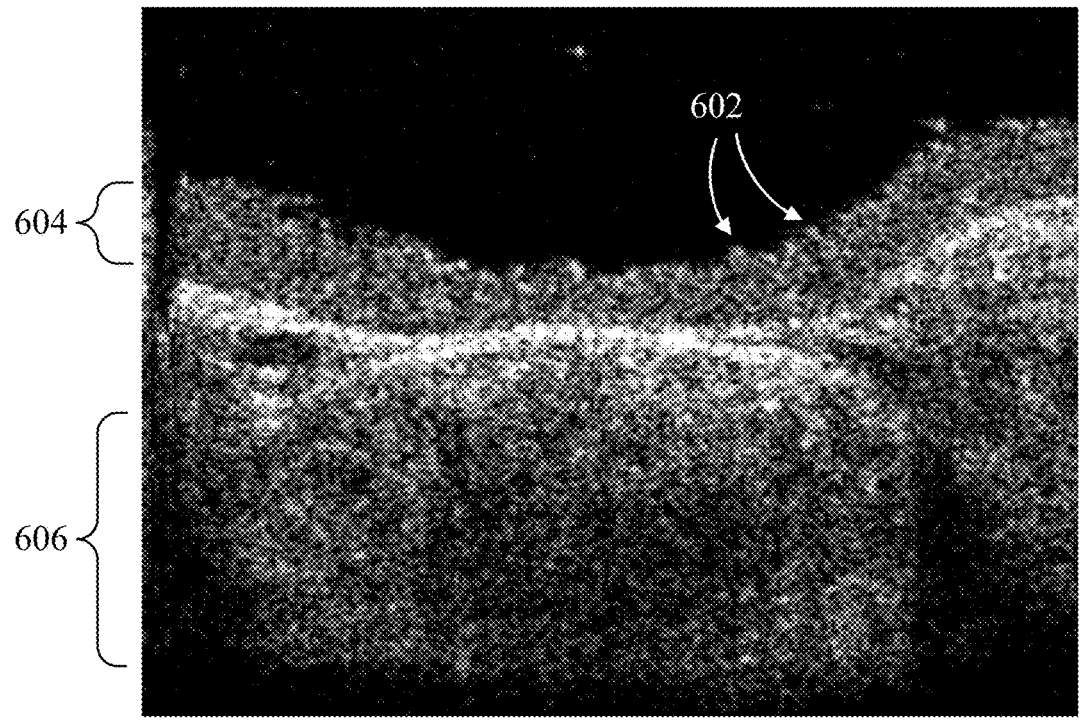
FIG. 6A shows an example of a cross-sectional image of ex vivo mouse trachea generated using a bench top optical coherence tomography system and a circularly apodized beam created using a rod mirror placed in the beam path.
Figure 6B:
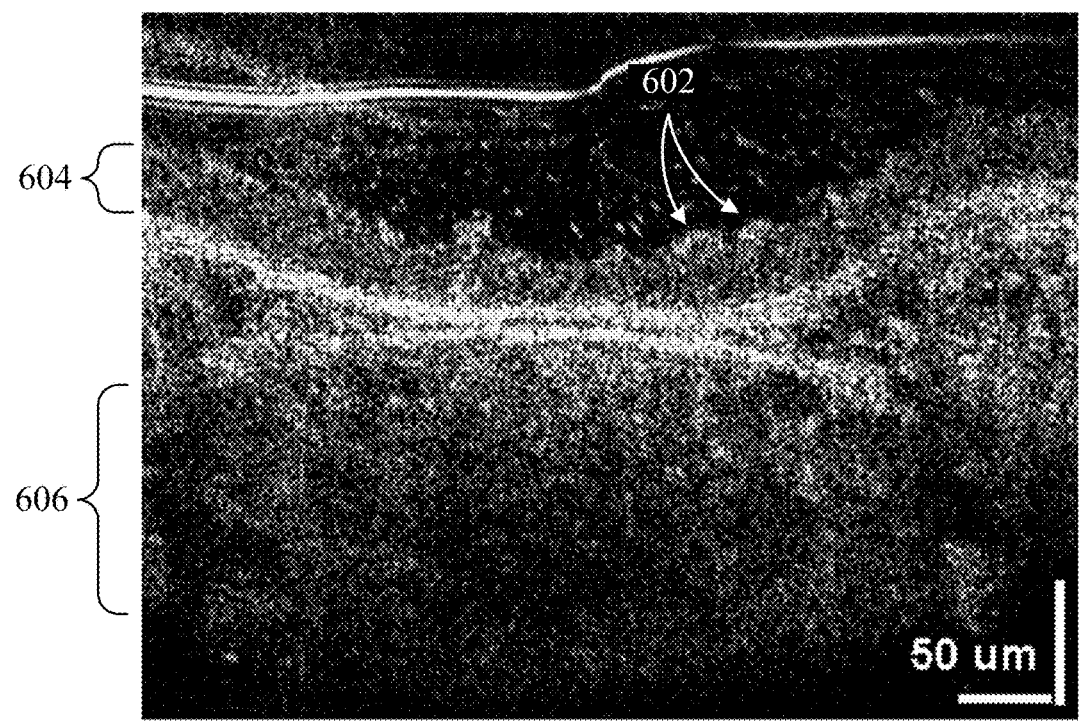
FIG. 6B shows an example of a cross-sectional image of ex vivo mouse trachea generated using an optical coherence tomography system and a circularly apodized beam created by optics that can be used for apodizing the optical imaging probe beam implemented in accordance with some embodiments of the disclosed subject matter.

FIG. 6A shows an example of a cross-sectional image of ex vivo mouse trachea generated using a bench top optical coherence tomography system and a circularly apodized beam created using a rod mirror placed in the beam path, and FIG. 6B shows an example of a cross-sectional image of ex vivo mouse trachea generated using an optical coherence tomography system and a circularly apodized beam created by optics that can be used for apodizing the optical imaging probe beam implemented in accordance with certain embodiments of the disclosed subject matter. The image in FIG. 6A was generated from data captured from an annular sample beam created by inserting a cylindrical rod mirror 2 millimeters (mm) in diameter directly in the sample beam path to divert a central portion of the beam, with the portion of the beam diverted by the cylindrical rod mirror being used to create a reference beam. The image in FIG. 6B was generated from data captured from an annular sample beam created using an APAR implemented in accordance with various embodiments of the disclosed subject matter, in which the optics had a 1 mm total diameter. The images of FIGS. 6A and 6B show cilia 602, a band 604 corresponding to epithelium, and a band 606 corresponding to cartilage rings.

Figure 7:
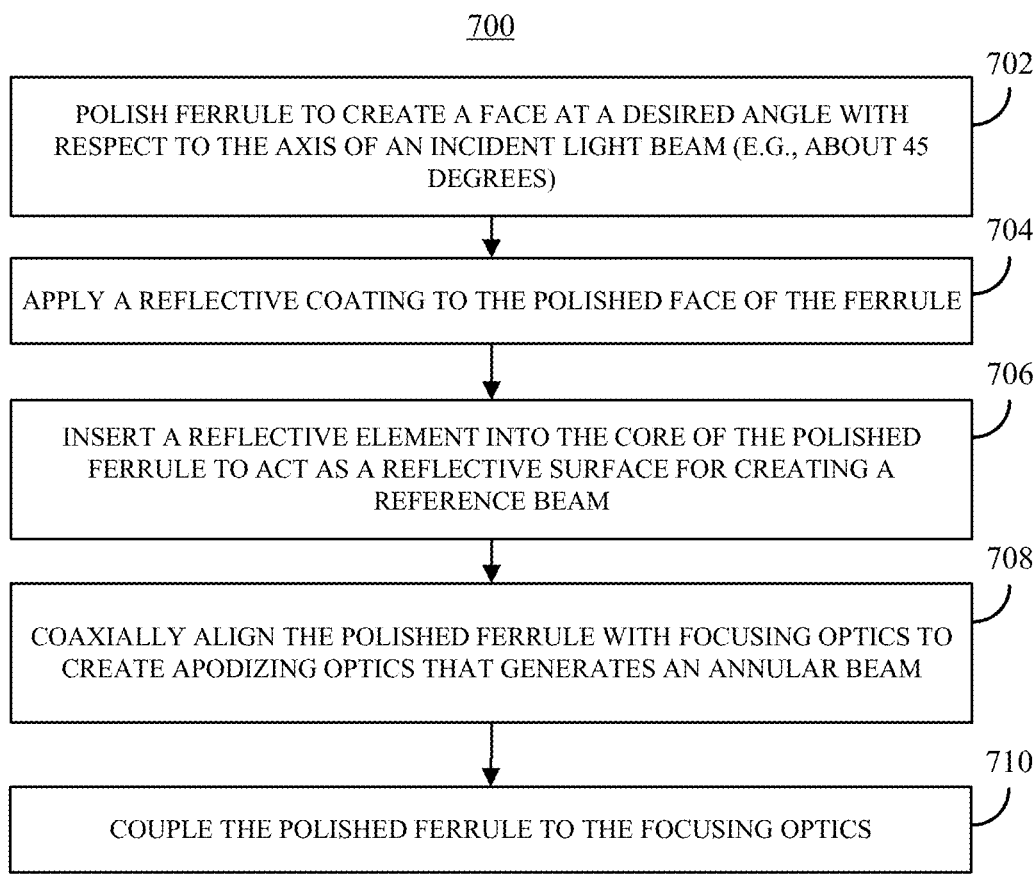
FIG. 7 shows an example of a process for fabricating optics that can be used for apodizing the optical imaging probe beam in accordance with some embodiments of the disclosed subject matter.

FIG. 7 shows an example 700 of a process for fabricating optics that can be used for apodizing the optical imaging probe beam in accordance with some embodiments of the disclosed subject matter. As shown in FIG. 7, process 700 can include polishing a ferrule to create a face at a desired angle with respect to the axis of an incident light beam. For example, as described above in connection with FIGS. 2A to 2C, a ferrule can be polished to have one face angled at about 45 degrees to a central axis of the ferrule. In some embodiments, any suitable technique or combination of techniques known to those skilled in the art may be used to polish the ferrule at 702 to remove a portion to create an angled face which optionally includes a face 224 for abutting the finished, polished ferrule against focusing element 210. The face 224 (e.g. see FIGS. 2A to 2D) may either be added after polishing by removing an end portion of the ferrule or by limiting the amount of polishing so that face 224 remains once polishing is complete. In some embodiments, the ferrule can be made from any suitable material, such as glass or ceramic. Alternatively, rather than starting with a ferrule, process 700 can start with another element, such as a slug of metal, a glass rod, a plastic rod, a ceramic rod, a manufactured metal tube (e.g., having a similar profile to a cannula of a hypodermic needle), bulk material (e.g., polymer, metal, etc.) for 3D printing, etc.

At 704, process 700 can include applying a reflective coating to the polished face of the ferrule. For example, the face can be coated with gold or another reflective material. In some embodiments, polishing of the face of the ferrule at 702 can render the polished face sufficiently reflective to render coating unnecessary. Note that the reflectivity of the face may vary based on the wavelength(s) of light being reflected, and that the polished face may be an appropriate reflector at some wavelengths but not others, and that a coating can be selected based on the wavelength(s) of light to be reflected.

At 706, process 700 can include inserting a reflective element into the core of the polished ferrule to act as a reflective surface for creating a reference beam from a central portion of the beam that enters the core. In some embodiments, the reflective element can be a portion of a fiber optic cable with an end that is polished and/or coated to create a surface capable of reflecting a substantial portion of the beam light impinging on the surface (e.g., enough to create a reference signal for an OCT device with which the optics being assembled are to be used). Note that it may be important to ensure that the face of reflective element 5 presents a face that is normal/perpendicular to the beam such that light impinging on the surface is reflected back toward the light source, rather than being diverted toward the inside wall of the ferrules core (e.g., aperture 218). In some embodiments, the reflective element can be inserted into the ferrule with any suitable adhesive, e.g. an adhesive that can be set (e.g., with UV light), and aligned using a device that can be used to ensure that the path length of a reference beam is approximately equal to the path length of the sample beam. For example, the ferrule can be held in place at a specific distance from an interferometer light source that simulates the path length of the sample beam, and the reflective element can be moved toward and/or away from the light source until a constructive interference of a maximum amplitude is observed. In such an example, when the reflective element is in such a position, it can be affixed in place (e.g., by shining UV light when using a UV-curing adhesive). In some embodiments, such as when the optics being assembled are to be used with a device that does not require a reference beam, or a device that produces a reference beam externally, the reflective element can be omitted, and correspondingly, step 706 can be omitted.

At 708, process 700 can include coaxially aligning the polished ferrule with focusing optics to create apodizing optics that generate an annular beam. In some embodiments, any suitable technique or combination of techniques can be used to coaxially align the polished ferrule with the focusing optics. For example, the various components can be placed within a tube (e.g., a steel tube) with relatively tight tolerances such that placement within the tube causes the components to be coaxially aligned.

At 710, process 700 can include coupling the polished ferrule to the focusing optics. In some embodiments, any suitable technique or combination of techniques can be used to couple the polished ferrule with the focusing optics. For example, various components can be secured to another component (e.g., a steel tube), and can be coupled via the other component. As another example, the polished ferrule can be coupled directly to the focusing optics via an adhesive (e.g., to secure face 224 to GRIN lens 210). As yet another example, the polished ferrule can be optically coupled to the focusing optics, rather than being physically coupled. In a more particular example, in some embodiments, a portion of the optics (e.g., optical fiber 202, focusing optics 210, etc.) can remain static, while the polished ferrule (e.g., ferrule 220) is rotated and the focusing optics can be physically separate from optical fiber 202. In some embodiments, 702-706 can be a process for fabricating an APAR, and 708-710 can be a process for coupling the APAR to optics of an optical imaging probe.

Figure 8:
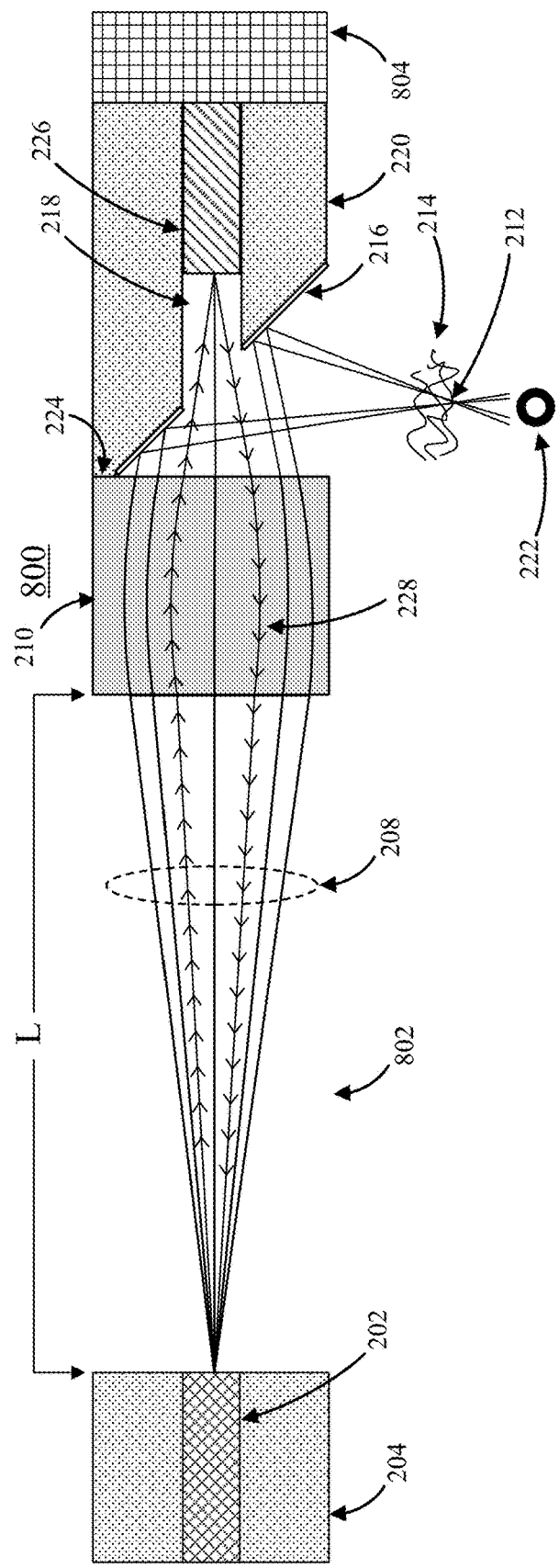
FIG. 8 shows another example of a cross-section view of optics that can be used for apodizing an optical imaging probe beam in accordance with some embodiments of the disclosed subject matter.

FIG. 8 shows an example 800 of a cross-section view of optics that can be used for apodizing an optical imaging probe beam in accordance with some embodiments of the disclosed subject matter. As shown in FIG. 8, in some embodiments, spacer 206 can be replaced by a gap 802 (e.g., filled with air, another gas, or a liquid). Additionally, in some embodiments, the APAR (e.g., including hollow element 220) can be coupled to a motor 804, which can the APAR and focusing element 210 around their central axis, while optical fiber 202 remains static.

Figure 9:
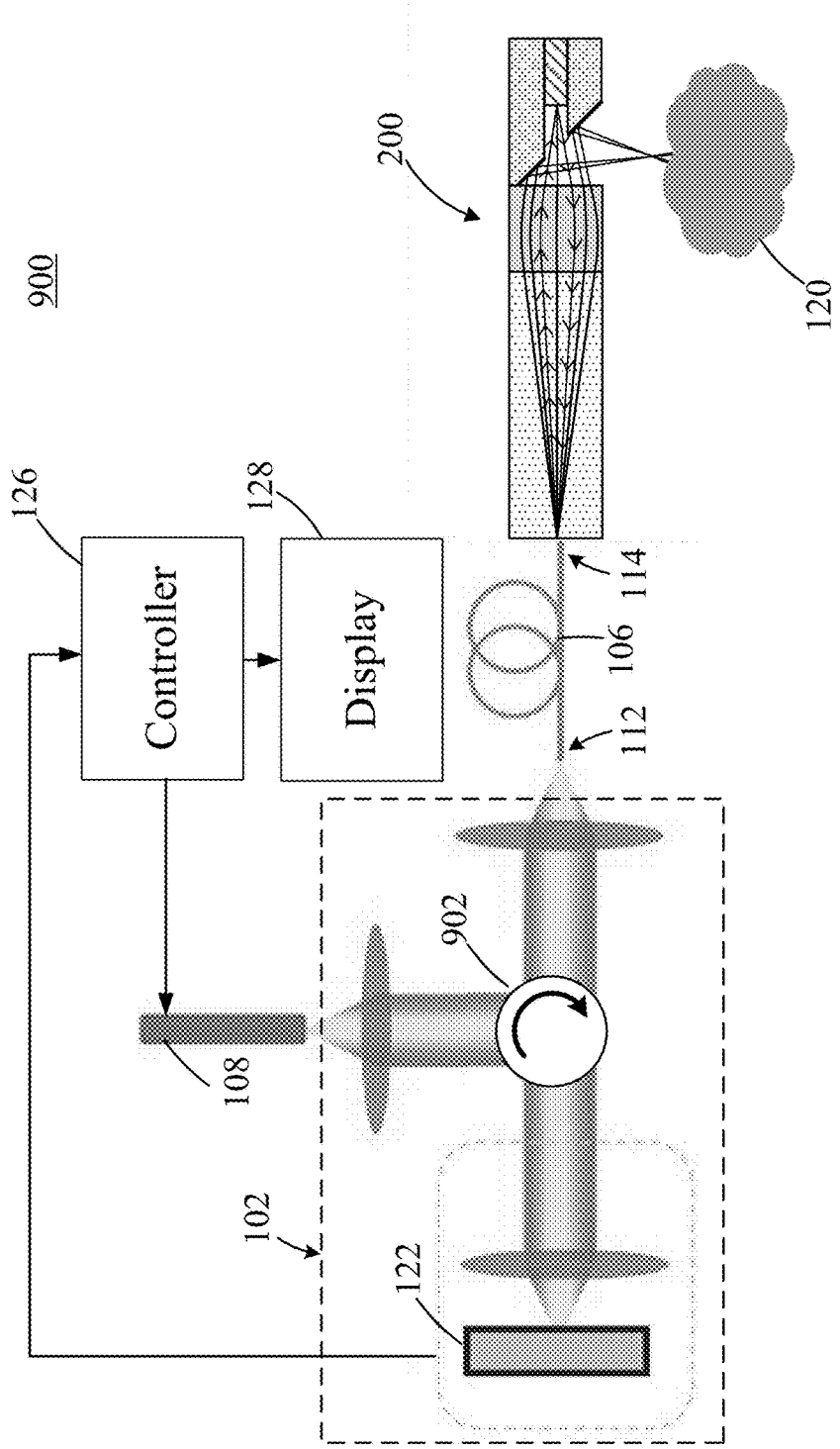
FIG. 9 shows an example of an OCT system with an optical imaging probe using optics described in accordance with some embodiments of the disclosed subject matter.

FIG. 9 shows an example 900 of an OCT system with an optical imaging probe using optics (including, e.g., an APAR) described in accordance with some embodiments of the disclosed subject matter. As shown in FIG. 9, imaging probe 104 may include optics 200, and reference reflector 124 may be omitted. In some embodiments, optical waveguide 106 can be a single mode fiber, and interference can occur when the sample beam reflected back toward optical waveguide 106 (e.g., by angled reflecting surface 216) and the reference beam reflected back toward optical waveguide 106 (e.g., by reference reflector 226) are transmitted together back toward optical assembly 102 by optical waveguide 106. In some embodiments, because a reference beam is generated by optics 200, beam splitter 110 can be replaced with another optical component 902, such as an optical circulator.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. Optics for apodizing an optical imaging probe beam, comprising:
   an optical fiber;
   a focusing element coaxially aligned with the optical fiber; and
   an element having a cylindrical bore and an angled reflective surface,
      a first portion of a beam being focused by the focusing element and entering the cylindrical bore, and
      a second portion of the beam being reflected at an angle by the angled reflective surface to produce a beam with a generally annular-shaped profile.

2. The optics of claim 1, wherein the focusing element is a cylindrical gradient index (GRIN) lens.

3. The optics of claim 1, wherein the element having the cylindrical bore comprises a ferrule,
   wherein the angled reflective surface comprises a polished surface.

4. The optics of claim 3, wherein the ferrule is ceramic.

5. The optics of claim 1, wherein the angled reflective surface comprises a reflective coating.

6. The optics of claim 5, wherein the reflective coating comprises gold.

7. The optics of claim 1, further comprising a spacer disposed between the optical fiber and the focusing element,
   wherein the beam expands in diameter within the spacer.

8. The optics of claim 7, wherein the spacer comprises glass.

9. The optics of claim 1, wherein the optical fiber is disposed within a ferrule.

10. The optics of claim 1, wherein a reflective surface is disposed within the cylindrical bore to reflect the first portion of the beam back toward the optical fiber.

11. The optics of claim 10, wherein the reflective surface comprises a face of a second optical fiber disposed within the cylindrical bore.

12. An optical coherence tomography (OCT) imaging system, comprising:
    a reference arm;

a light source; and apodizing optics for generating an apodized beam comprising:

an optical fiber coupled to the light source, a focusing element coaxially aligned with the optical fiber, and a cylindrical element coaxially aligned with the focusing element, the cylindrical element having a bore and an angled reflective surface, a first portion of a beam being focused by the focusing element and entering the bore, and a second portion of the beam being reflected at an angle by the angled reflective surface to produce a beam with a generally annular-shaped profile.

13. The OCT imaging system of claim 12, wherein the reference arm comprises a reference reflective surface disposed within the bore to reflect the first portion of the beam back toward the optical fiber.

14. The OCT imaging system of claim 12, wherein the angled reflective surface is at a 45 degree angle with respect to a long axis of the cylindrical element.

15. The OCT imaging system of claim 12, wherein the focusing element is a cylindrical gradient index (GRIN) lens.

16. The OCT imaging system of claim 12, wherein the angled reflective surface comprises a reflective coating.

17. The OCT imaging system of claim 12, wherein the optics are rotatably mounted within the OCT imaging system.

18. The OCT imaging system of claim 12, further comprising a catheter including the apodizing optics.

19. The OCT imaging system of claim 12, further comprising a spacer disposed between the optical fiber and the focusing element, wherein the beam expands in diameter within the spacer.

20. The OCT imaging system of claim 12, wherein the cylindrical element further comprises a truncated face which abuts the focusing element.

* * * * *